(12) United States Patent
Benson et al.

(10) Patent No.: US 12,055,251 B2
(45) Date of Patent: Aug. 6, 2024

(54) FLUID COUPLINGS

(71) Applicant: Colder Products Company, Roseville, MN (US)

(72) Inventors: Timothy C. Benson, Andover, MN (US); Jacob D. Fellows, Blaine, MN (US); Gary J. Harris, Maple Grove, MN (US); Andrew M. Quick, St. Paul, MN (US); Loi T. Truong, Savage, MN (US)

(73) Assignee: Colder Products Company, Roseville, MN (US)

( * ) Notice: Subject to any disclaimer, the term of this patent is extended or adjusted under 35 U.S.C. 154(b) by 0 days.

(21) Appl. No.: 17/965,399

(22) Filed: Oct. 13, 2022

(65) Prior Publication Data

US 2023/0122306 A1    Apr. 20, 2023

Related U.S. Application Data (60) Provisional application No. 63/344,692, filed on May 23, 2022, provisional application No. 63/256,983, filed on Oct. 18, 2021.

(51) Int. Cl.
*F16L 37/10* (2006.01)
*F16L 37/46* (2006.01)
(Continued)

(52) U.S. Cl.
CPC ............... *F16L 37/46* (2013.01); *F16L 37/10* (2013.01); *F16L 37/0842* (2013.01);
(Continued)

(58) Field of Classification Search
CPC .............. A61M 39/1011; A61M 39/26; A61M 2039/1044; A61M 2039/1027; A61M 39/18; A61M 2039/267; A61M 2205/273; F16L 37/10–20; F16L 37/23; F16L 37/34; F16L 37/35; F16L 37/107; F16L 2201/44; F16L 37/133; F16L 37/1215; F16L 37/121; F16L 37/26; F16L 37/44; F16L 37/36; F16L 37/0982; F16L 37/0985; F16L 37/0842; Y10T 137/87941; Y10T 137/9029; Y10T 137/87925–87973
USPC ............ 137/614–614.6, 798; 603/5.04, 5.01, 603/6.09, 4.01, 533–536, 905; 128/887, 128/200.24, 202.16, 204.18, 207.14, 128/200.26, 912

See application file for complete search history.

(56) References Cited

U.S. PATENT DOCUMENTS

| | | | | |
|---|---|---|---|---|
| 4,366,816 A | * | 1/1983 | Bayard | A61M 39/26 604/905 |
| 4,380,310 A | * | 4/1983 | Schneiter | B67D 3/045 222/525 |

(Continued)

OTHER PUBLICATIONS

International Search Report and Written Opinion in International Appln. No. PCT/US2022/046550, mailed on Jan. 31, 2023, 17 pages.

*Primary Examiner* — Craig J Price
(74) *Attorney, Agent, or Firm* — Fish & Richardson P.C.

(57) ABSTRACT

This document describes fluid handling couplings. For example, this document describes fluid handling couplings that include manually openable valves and that are configured for aseptic fluid handling usage. In some embodiments, the valves are manually openable by rotation of a collar of the fluid handling couplings.

8 Claims, 13 Drawing Sheets

(51) Int. Cl.
*F16L 37/084* (2006.01)
*F16L 37/098* (2006.01)

(52) U.S. Cl.
CPC ....... *F16L 37/0982* (2013.01); *F16L 37/0985* (2013.01); *F16L 2201/60* (2013.01); *Y10T 137/9029* (2015.04)

(56) References Cited

U.S. PATENT DOCUMENTS

| | | | | |
|---|---|---|---|---|
| 5,433,410 A * | 7/1995 | Foltz | .................. | F16K 3/26 |
| | | | | 251/351 |
| 5,482,083 A * | 1/1996 | Jenski | .................. | F16L 37/35 |
| | | | | 285/307 |
| 7,080,665 B2 * | 7/2006 | Whall | .................. | F16L 37/0841 |
| | | | | 137/625.48 |
| 7,546,857 B2 * | 6/2009 | Chadbourne | ........ | B67D 1/0835 |
| | | | | 141/354 |
| 8,042,571 B2 * | 10/2011 | Eccles | .................. | F16L 37/34 |
| | | | | 137/614.04 |
| 8,210,501 B2 * | 7/2012 | Lee | .................. | F16K 15/20 |
| | | | | 251/285 |
| 8,251,346 B2 * | 8/2012 | Stroup | .................. | A61M 39/10 |
| | | | | 251/149.6 |
| 8,764,068 B2 | 7/2014 | Frick et al. | | |
| 8,910,919 B2 * | 12/2014 | Bonnal | .............. | A61M 39/1011 |
| | | | | 604/533 |
| 10,022,532 B2 * | 7/2018 | Burdge | .................. | A61M 39/18 |
| 10,569,073 B2 * | 2/2020 | Hallisey | .............. | F01M 11/0408 |
| 10,871,249 B1 * | 12/2020 | Burns | ................ | F01M 11/0408 |
| 11,739,872 B2 * | 8/2023 | Casura | .................. | A61M 39/18 |
| | | | | 251/149.1 |
| 2005/0101939 A1 | 5/2005 | Mitchell | | |
| 2010/0019487 A1 | 1/2010 | Decler et al. | | |
| 2017/0106181 A1 | 4/2017 | Bonaldo et al. | | |
| 2019/0137021 A1 | 5/2019 | Downs et al. | | |
| 2021/0199220 A1 | 7/2021 | Truong | | |

\* cited by examiner

SECTION A-A

FLUID COUPLINGS

CROSS-REFERENCE TO RELATED APPLICATIONS

This application claims the benefit of U.S. Provisional Application Ser. No. 63/256,983, filed Oct. 18, 2021, and U.S. Provisional Application Ser. No. 63/344,692, filed May 23, 2022. The disclosure of the prior application is considered part of (and is incorporated by reference in) the disclosure of this application.

BACKGROUND

1. Technical Field

This document relates to fluid handling couplings.

2. Background Information

Fluid handling components such as fluid couplings allow fluid communication between two or more components. Some fluid couplings include features that allow male and female components (or genderless fluid coupling components) to be quickly connected or disconnected, and may include one or more internal valve components that selectively block or allow flow of fluid through the coupling.

SUMMARY

This document describes a number of fluid coupling devices for fluid systems and methods. In some embodiments, the fluid coupling devices can be implemented as single-use or multi-use, aseptic fluid coupling connection devices. In the context of this disclosure, the term "fluid" means any substance that can be made to flow including, but is not limited to, liquids, gases, granular or powdered solids, mixtures or emulsions of two or more fluids, suspensions of solids within liquids or gases, gels, vapors, steam, mists, etc., without limitation.

In particular embodiments, the fluid coupling devices described herein are single-use devices because, after the two portions of the coupling (also referred to herein as "coupling halves" and/or "connectors") are connected to each other, the coupled portions are designed to resist uncoupling. For example, such single-use coupling devices are equipped with one or more mechanical components that operate like locks to maintain the two portions of the coupling in the coupled state. Hence, in these particular embodiments, the fluid coupling devices provided herein are structurally configured to be single-use connection devices so that, after the single-use coupling halves have been connected to each other, they cannot be operably disconnected from each other (as such, preserving the sterility or biological integrity of the system/flow path/etc.).

The fluid coupling devices described herein include internal valves that can be manually opened and/or closed.

Additionally, the fluid coupling devices described herein can be configured as "aseptic" coupling devices in that can be connected to each other while inhibiting biological contamination from migrating into the flow paths. Such an "aseptic" coupling will also serve to limit the exposure of the fluid to the surrounding environment.

Further, in some embodiments the fluid coupling devices can be configured as genderless couplings. That is, the two coupling portions can be designed exactly alike (or substantially alike) so that there is no male or female coupling halves as in many conventional fluid coupling designs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes fluid handling couplings. For example, this document describes fluid handling couplings that include manually openable and/or closeable valves and that are configured for single-use aseptic fluid handling usage contexts. In particular embodiments, the fluid coupling devices described herein are single-use devices because, after two of the couplings (also referred to herein as "coupling halves" and/or "connectors") are connected to each other, the coupled portions are designed to resist uncoupling.

As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies. As used herein, the term "aseptic" refers to any process that maintains a sterilized surface or volume. As used herein, the term "fluid" means any substance that can be made to flow including, but is not limited to, liquids, gases, granular or powdered solids, mixtures or emulsions of two or more fluids, suspensions of solids within liquids or gases, etc.

Figure 1:
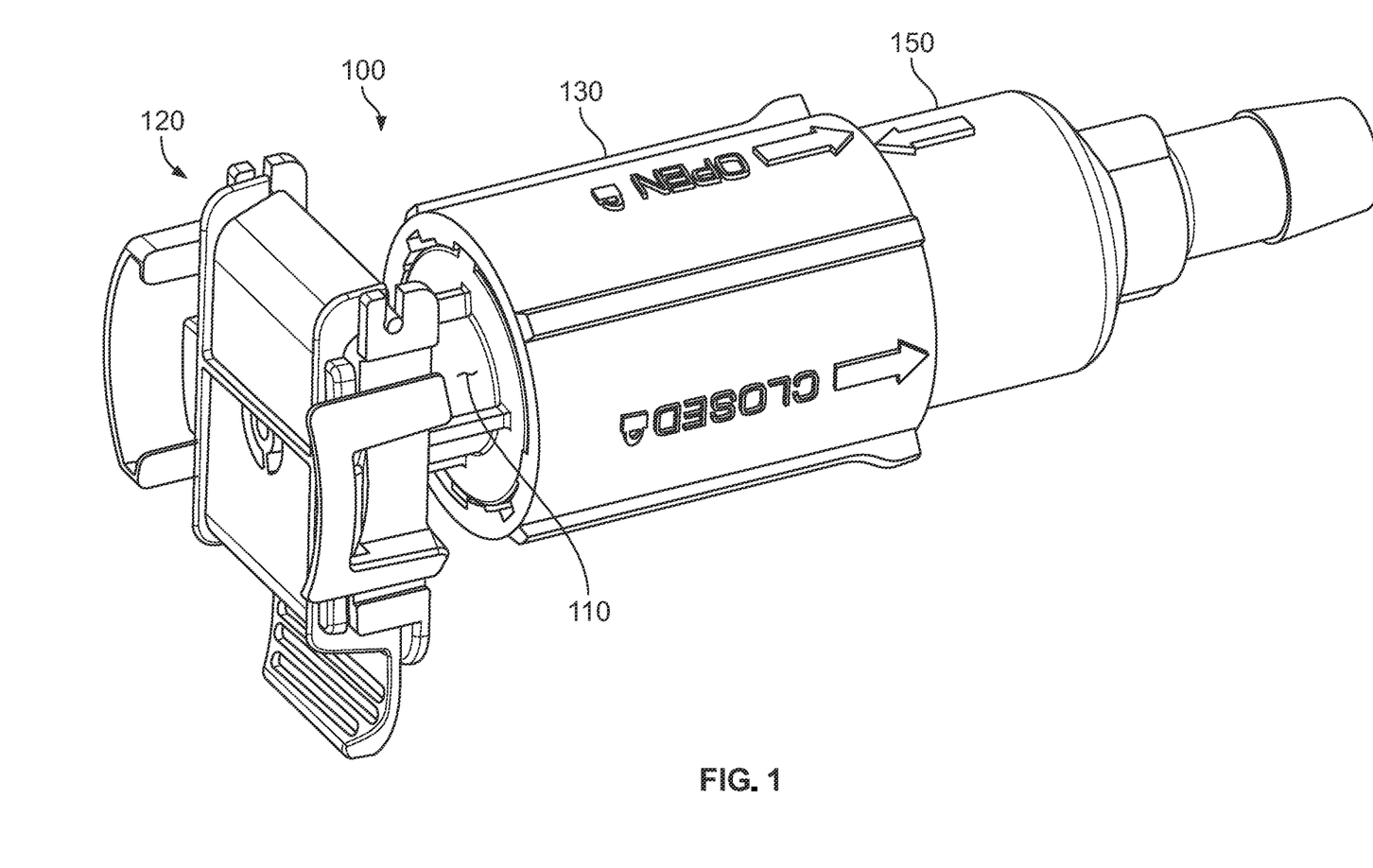
FIG. 1 is a perspective view of an example fluid coupling in accordance with some embodiments provided herein.
Figure 2:
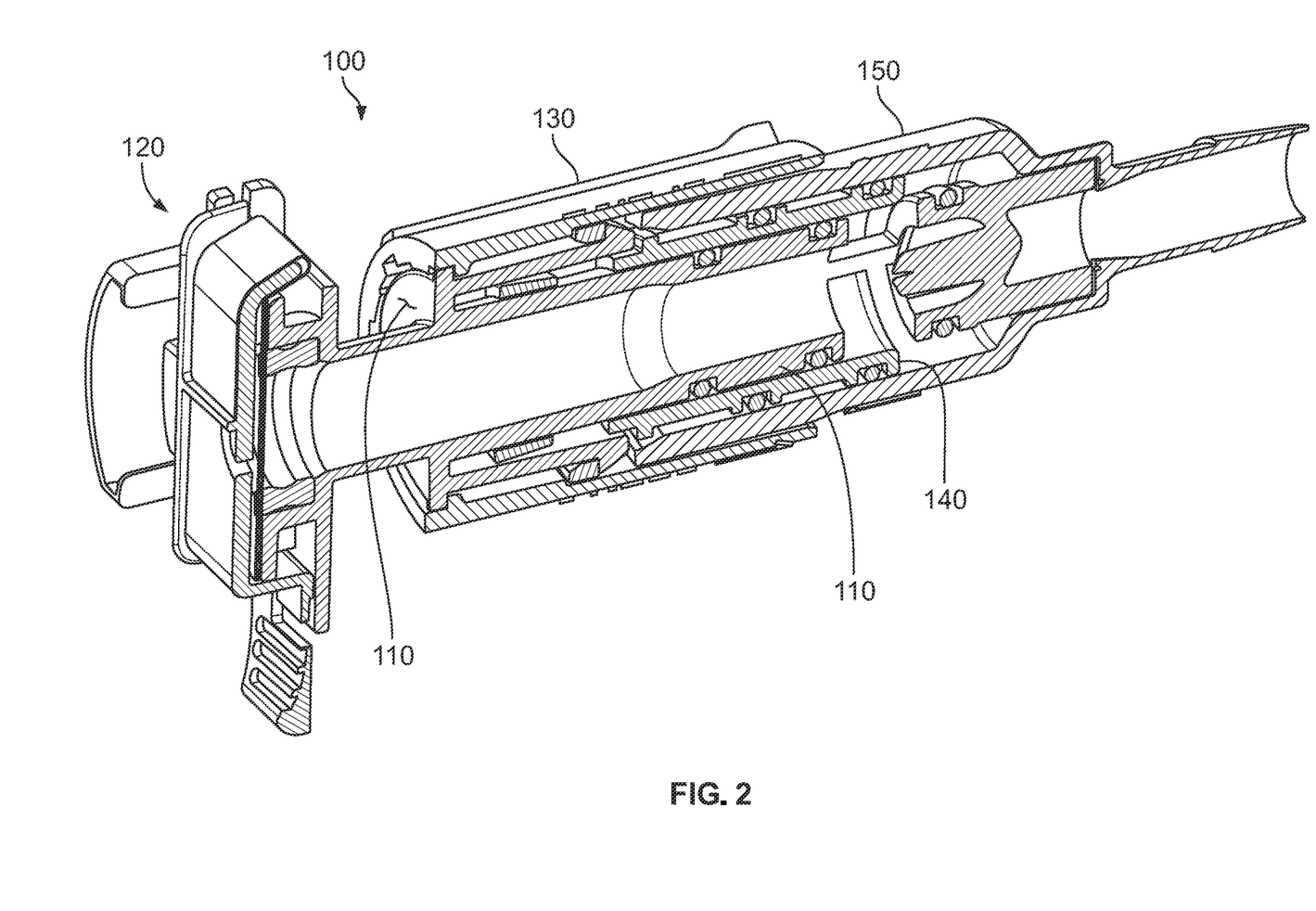
FIG. 2 is longitudinal cross-sectional view of the fluid coupling of FIG. 1.

FIGS. 1 and 2 show an example fluid coupling device 100. The fluid coupling device 100 includes a main body 110, an aseptic attachment structure 120 (including a removable membrane), a collar 130, a valve shuttle member 140, and a termination member 150. The removable membrane can be a porous material that allows gasses to pass through while preventing bio-contaminants and/or particulate from passing through. The collar 130 is rotatably coupled to the main body 110 and the termination member 150. Rotation of the collar 130 relative to the main body 110 drives longitudinal translational movements of the valve shuttle member 140 relative to the main body 110 and the termination member 150 between an open position (as shown) in which fluid can flow through the fluid coupling device 100, and a closed position in which the valve shuttle member 140 blocks fluid from flowing into and/or through the main body 110.

The materials from which one or more of the components of the fluid coupling device 100 (and other fluid couplings described herein) can be made include thermoplastics. In particular embodiments, the materials from which the components of the fluid coupling device 100 are made are thermoplastics, such as, but not limited to, acetal, polycarbonate, polysulfone, polyether ether ketone, polysulphide, polyester, polyvinylidene fluoride (PVDF), polyethylene, polyphenylsulfone (PPSU; e.g., Radel®), acrylonitrile butadiene styrene (ABS), polyetherimide (PEI; e.g., Ultem®), polypropylene, polyphenylene, polyaryletherketone, and the like, and combinations thereof. In some embodiments, the thermoplastics can include one or more fillers such as, but not limited to, glass fiber, glass bead, carbon fiber, talc, etc.

In some embodiments, the materials from which one or more of the components of the fluid coupling device 100 (and other fluid couplings described herein) are made of include metals such as, but not limited to copper, stainless steel, brass, aluminum, plated steel, zinc alloys, and the like. In particular embodiments, the fluid coupling device 100 is metallic-free.

In some embodiments, as described further below, the fluid coupling device 100 can include one or more seal members. In some embodiments, the seal members of the fluid coupling device 100 (and the other fluid couplings described herein) can comprise materials such as, but not limited to, silicone, fluoroelastomers (FKM), ethylene propylene diene monomer (EPDM), thermoplastic elastomers (TPE), bung, buna-N, thermoplastic vulcanizates (TPV), and the like. The cross-sectional shape of such seal members can be circular, D-shaped, X-shaped, square, rectangular, U-shaped, multi-lobed, L-shaped, V-shaped, hourglass-shaped, and the like, or any other suitable shape, without limitation.

The aseptic attachment structure 120 is configured to facilitate an aseptic connection to a second compatible fluid coupling device (not shown). In some embodiments, the second fluid coupling device can be another fluid coupling device 100. In some embodiments, the second fluid coupling device can be a different type of fluid coupling (as long as it has an aseptic attachment structure that is compatible with the aseptic attachment structure 120).

In some embodiments, the collar 130 can be rotated to open and/or close the valve shuttle member 140 as many times as a user desires. In some embodiments, the collar 130 can only be rotated to the position the valve shuttle member 140 in its open position a single time. In such a case, the valve shuttle member 140 can latch to be detained in its open position.

In some embodiments, the connection sequence for mating the fluid coupling device 100 to a second compatible aseptic fluid coupling is as follows. First, the fluid coupling device 100 starts with its valve shuttle member 140 in its closed position. Then, using the aseptic attachment structure 120, an aseptic connection is made between the fluid coupling device 100 and a second compatible aseptic fluid coupling. Then, the user rotates the collar 130 to translate the valve shuttle member 140 to its open position to allow fluid to flow through the fluid coupling device 100.

Figure 3:
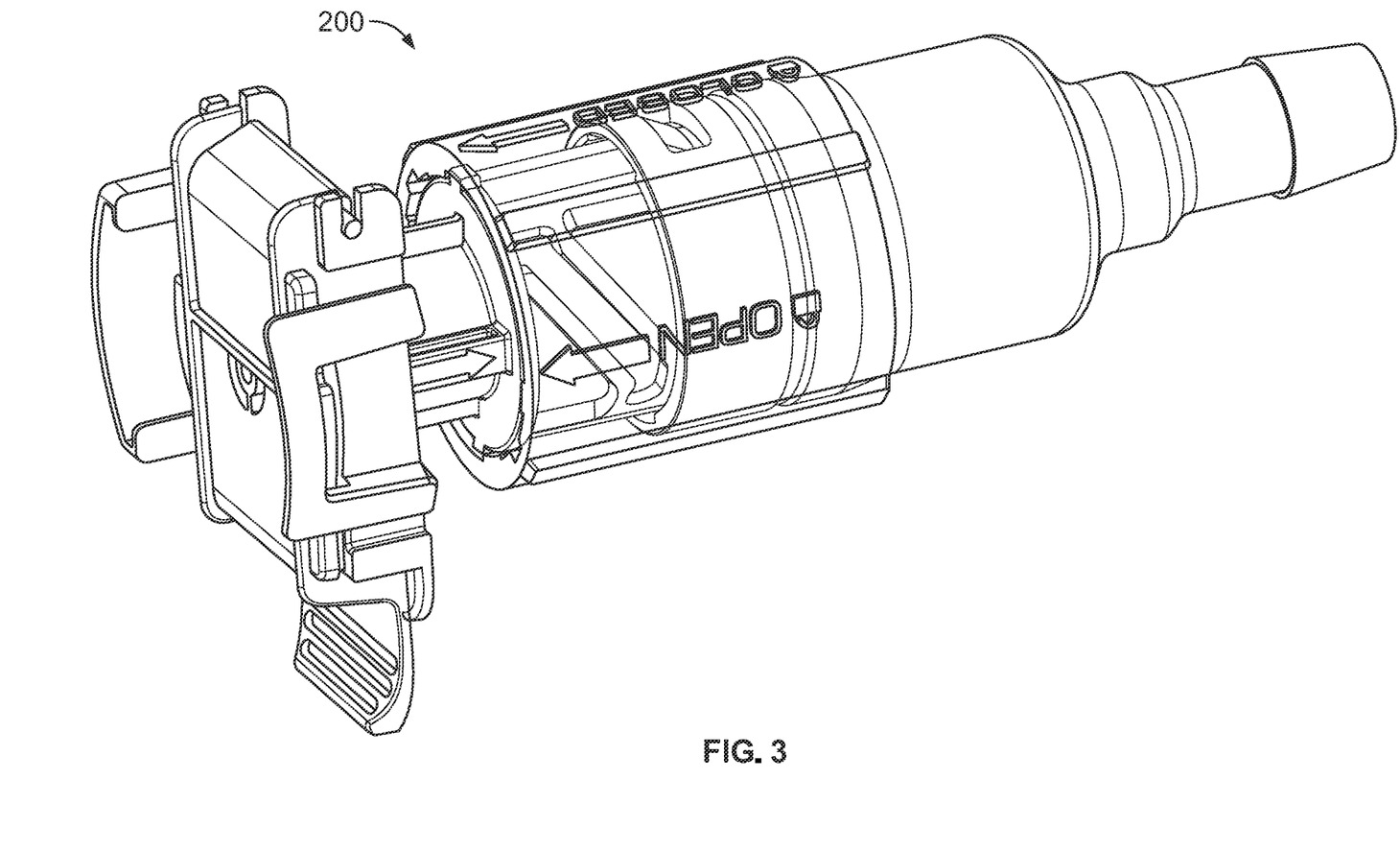
FIG. 3 is a perspective view of another example fluid coupling in accordance with some embodiments provided herein.
Figure 4:
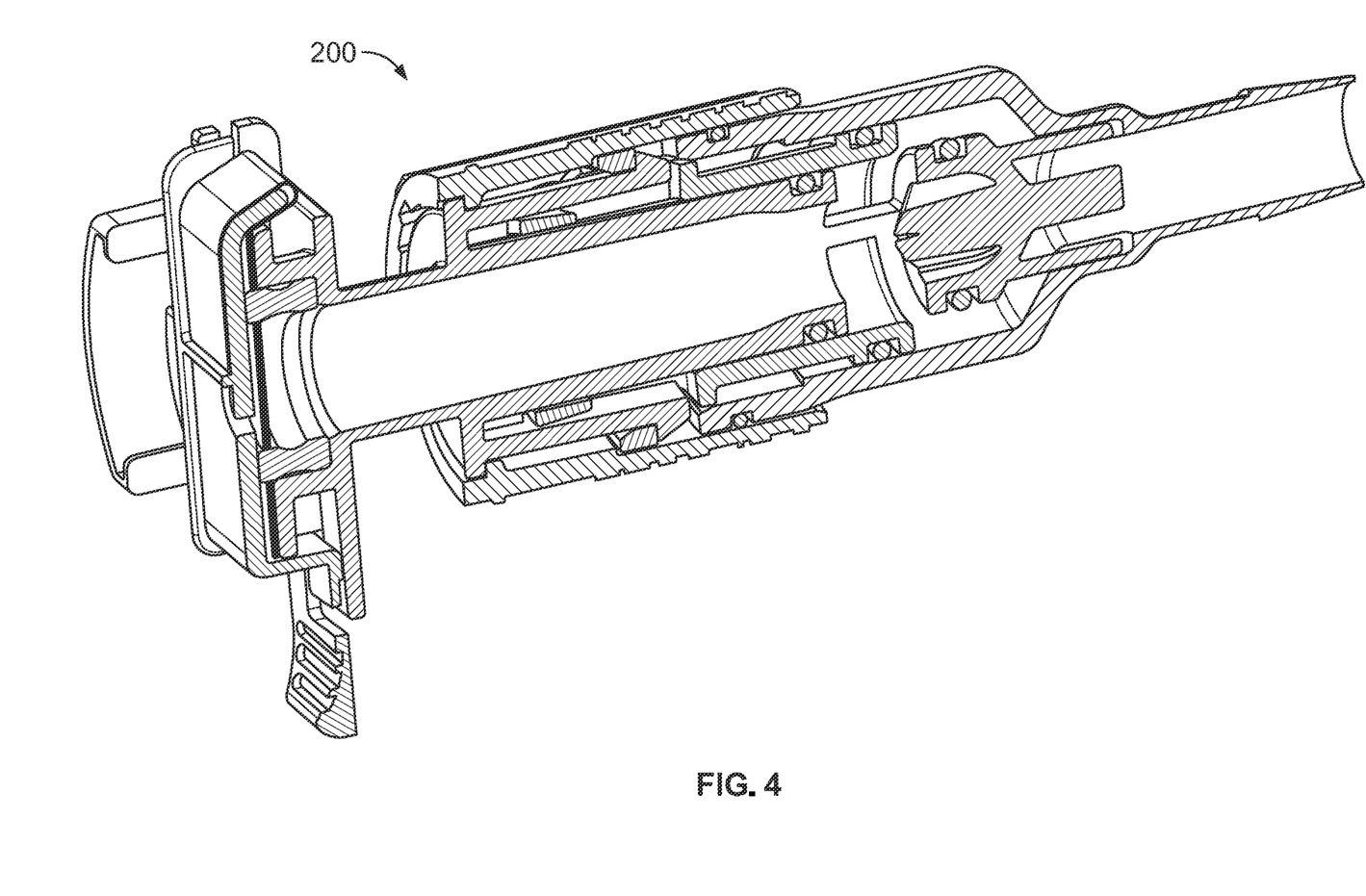
FIG. 4 is longitudinal cross-sectional view of the fluid coupling of FIG. 3.

FIGS. 3 and 4 show another example fluid coupling device 200. The fluid coupling device 200 can function in the same manner as the fluid coupling device 100 described above.

FIGS. 5-9 illustrate another example fluid coupling device 300. The fluid coupling device 300 includes a main body 310, an aseptic attachment structure 320 (including a protective cover and a removable membrane that is removably attached to a front face of the main body 310), a collar 330, a valve shuttle member 340, and a termination member 350.

Figure 7:
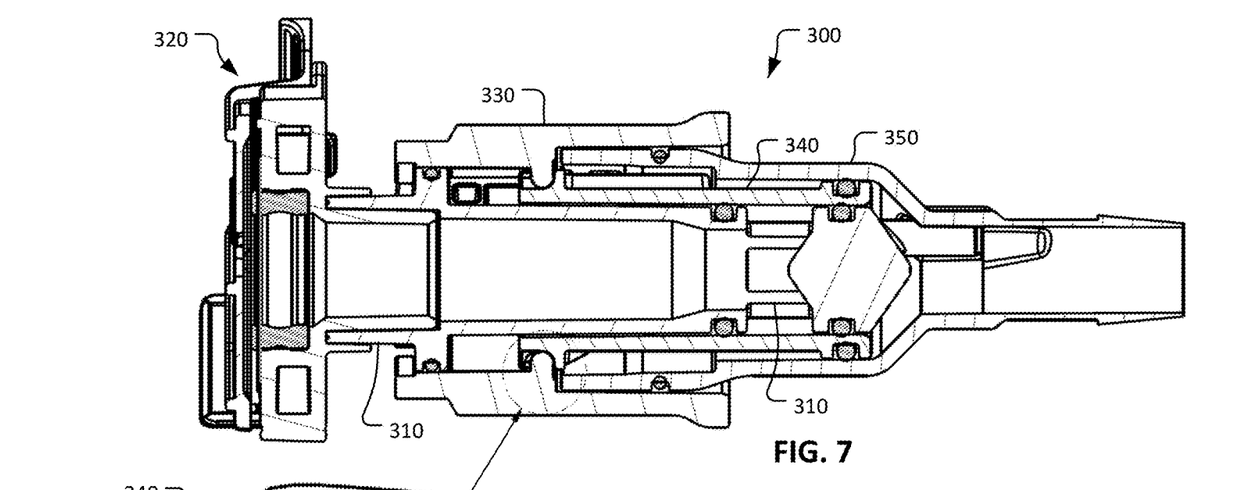
FIG. 7 is a longitudinal cross-sectional view of the fluid coupling of FIG. 5 with the shuttle valve in a closed configuration.
Figure 9:
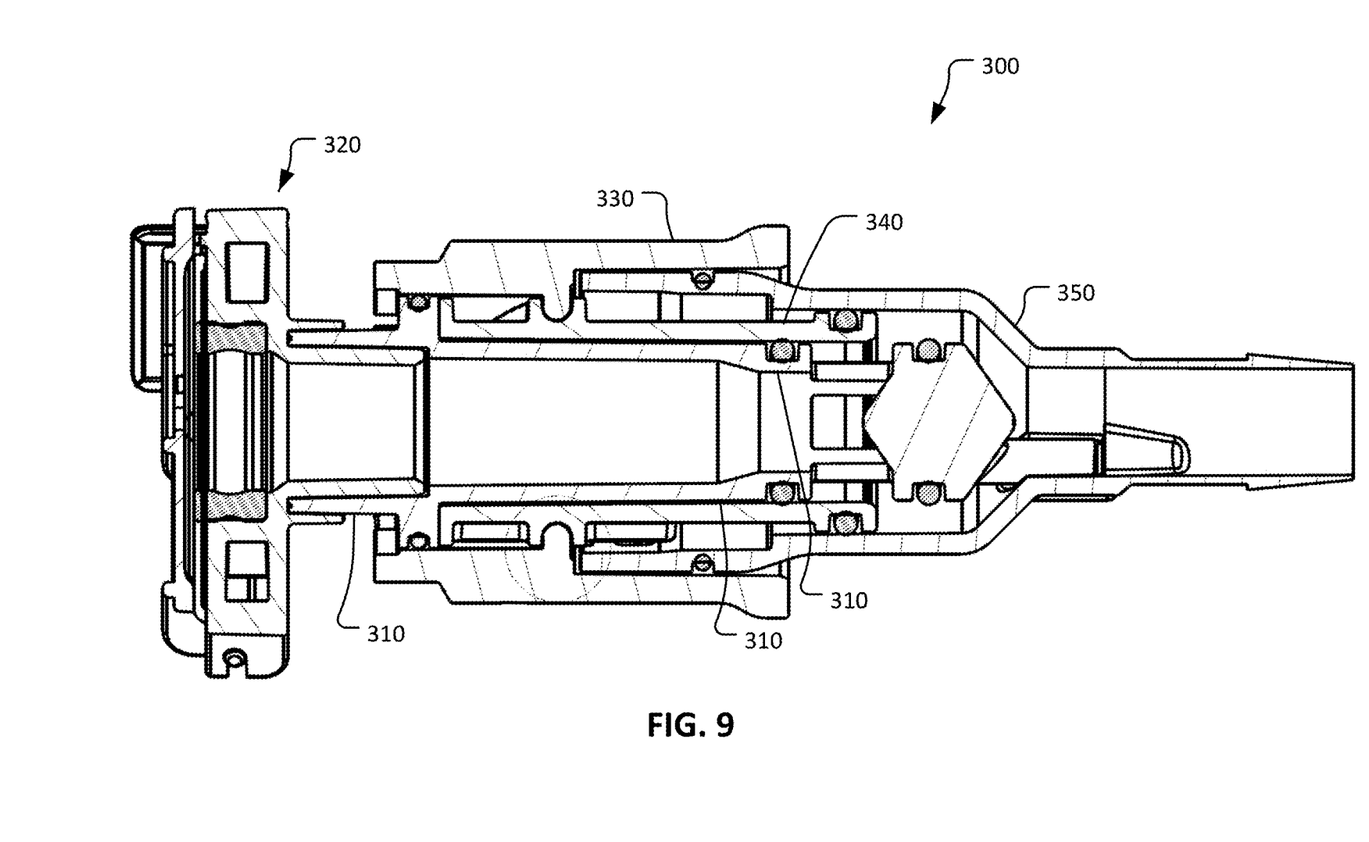
FIG. 9 is a longitudinal cross-sectional view of the fluid coupling of FIG. 5 with the shuttle valve in an open configuration.
Figure 10:
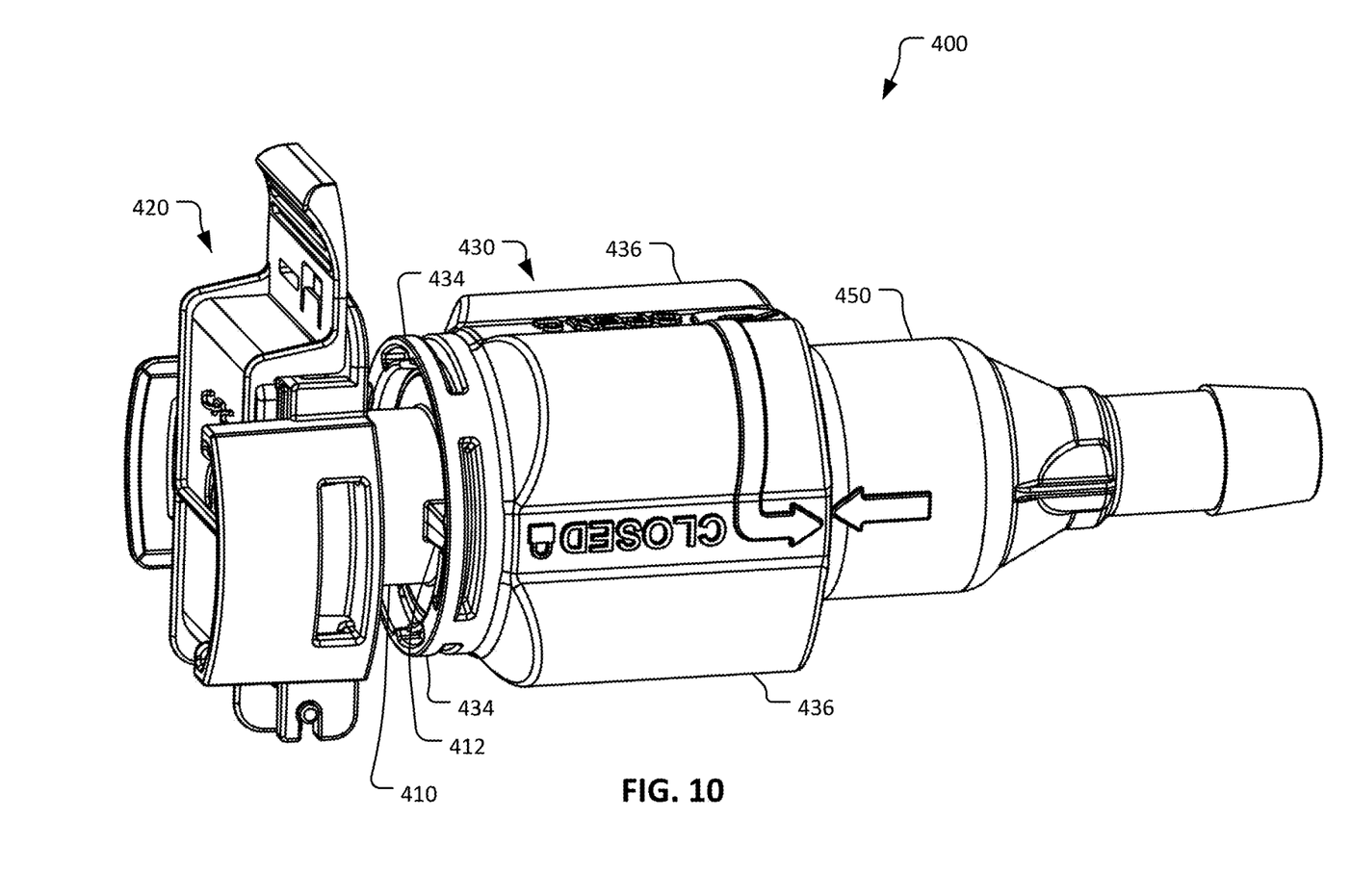
FIG. 10 is a perspective view of another example fluid coupling in accordance with some embodiments provided herein.

The collar 330 is rotatably coupled to the main body 310 and the termination member 350. Rotation of the collar 330 relative to the main body 310 drives longitudinal translational movements of the valve shuttle member 340 relative to the main body 310 and the termination member 350. Accordingly, rotation of the collar 330 moves the valve shuttle member 340 between a closed position (as shown in FIG. 7) in which the valve shuttle member 340 blocks fluid from flowing into and/or through the main body 310 and an open position (as shown in FIG. 9) in which fluid can flow through the fluid coupling device 300.

The aseptic attachment structure 320 is configured to facilitate an aseptic connection to a second compatible fluid coupling device (not shown). In some embodiments, the second fluid coupling device can be another fluid coupling device 300. In some embodiments, the second fluid coupling device can be a different type of fluid coupling (as long as it has an aseptic attachment structure that is compatible with the aseptic attachment structure 320).

In some embodiments, the collar 330 can be rotated to open and/or close the valve shuttle member 340 as many times as a user desires. In some embodiments, the collar 330 can only be rotated to the position the valve shuttle member 340 in its open position a single time. In such a case, the valve shuttle member 340 can latch/lock to be detained in its open position.

In the depicted embodiment, the collar 330 includes two flexible arms 334 (FIGS. 5 and 6) that interface with two projections 312 that extend radially from the main body 310.

Figure 5:
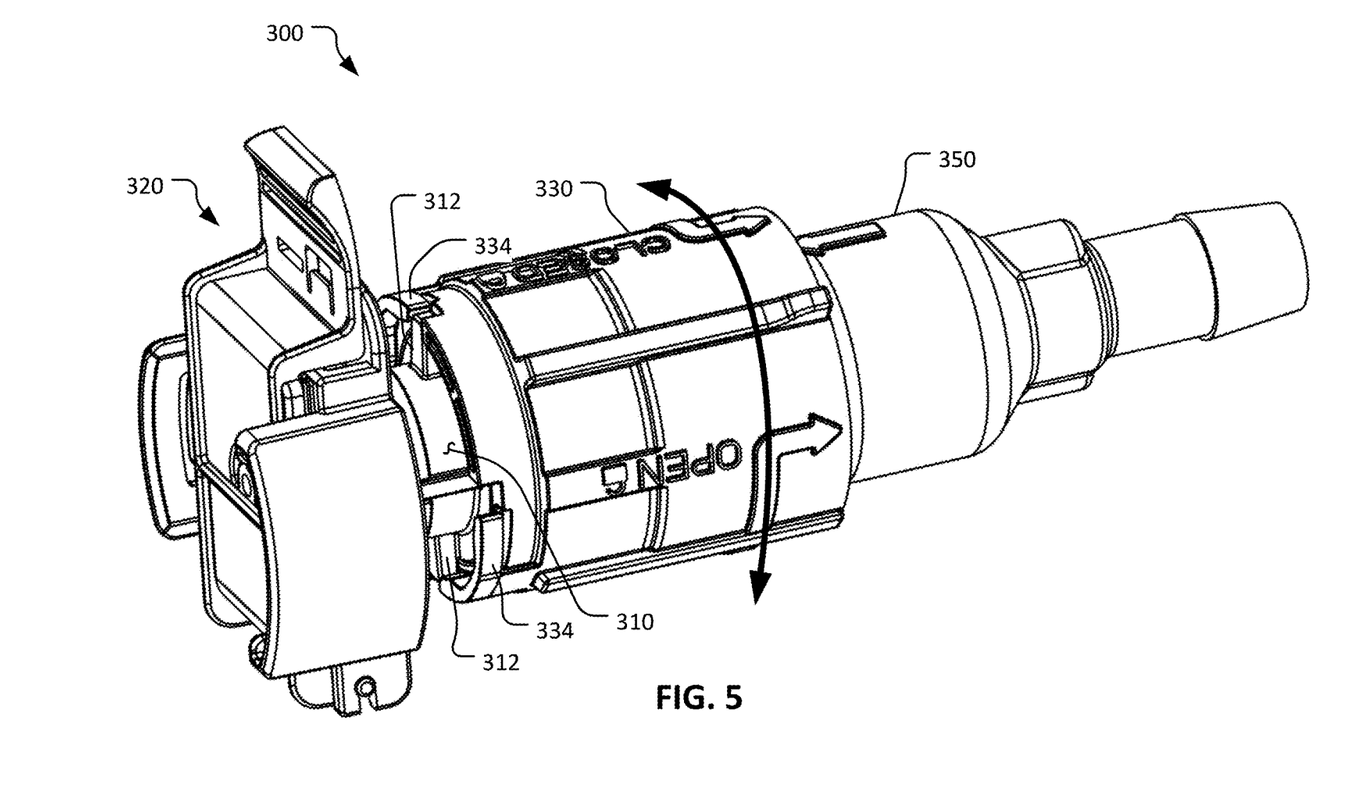
FIG. 5 is a perspective view of another example fluid coupling in accordance with some embodiments provided herein.
Figure 6:
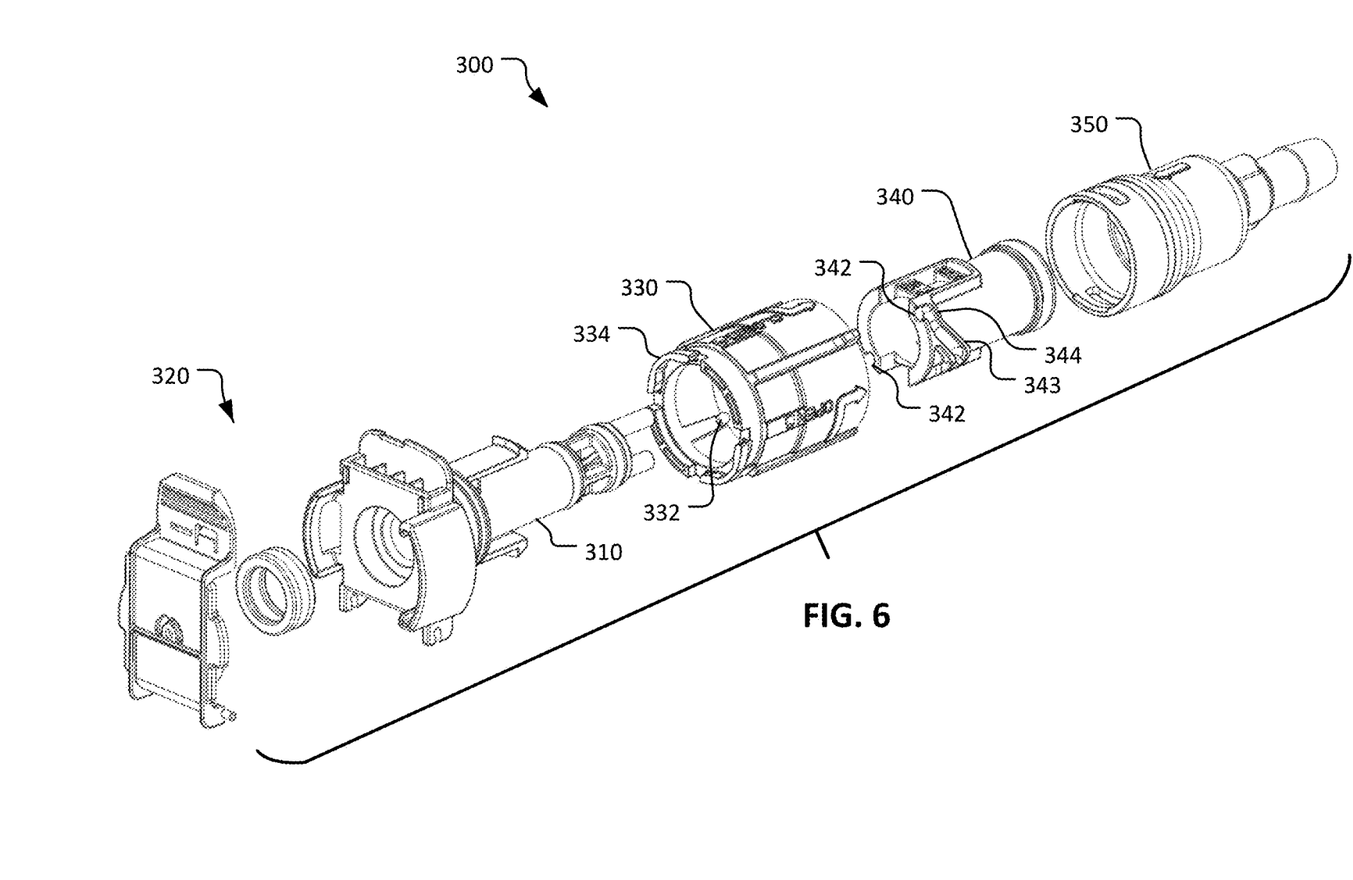
FIG. 6 is an exploded perspective view of the fluid coupling of FIG. 5.

The interactions between the projections 312 and the flexible arms 334 create a detent mechanism that is reversible (applying enough force can overcome the detent), and/or a latching mechanism that is locked and not reversible, between the collar 330 and the main body 310 at the end limits of rotational travel of the collar 330 relative to the main body 310. The end limits of rotational travel of the collar 330 relative to the main body 310 also correspond to the fully open and fully closed positions of the valve shuttle member 340 relative to the main body 310 and the termination member 350.

In some embodiments, the connection sequence for mating the fluid coupling device 300 to a second compatible aseptic fluid coupling is as follows. First, the fluid coupling device 300 starts with its valve shuttle member 340 in its closed position (FIG. 7). Then, using the aseptic attachment structure 320, an aseptic connection is made between the fluid coupling device 300 and a second compatible aseptic fluid coupling. Then, the user rotates the collar 330 to translate the valve shuttle member 340 to its open position (FIG. 9) to allow fluid to flow through the fluid coupling device 300.

Figure 8:
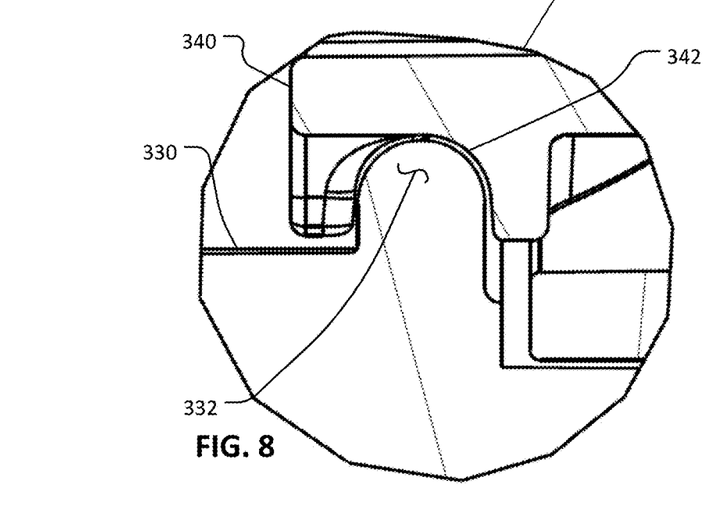
FIG. 8 is an enlarged cutaway view of a portion of FIG. 7.

As the collar 330 is rotated, two projections 332 on the collar 330 slide along two corresponding grooves 342 defined by the valve shuttle member 340. As shown in FIG. 8, for example, in the depicted embodiment the end portions of the projections 332 are hemispherical and the grooves 342 have a corresponding semi-circular cross-sectional shape. This arrangement provides a semi-circular line contact between the collar 330 and the valve shuttle member 340 that minimizes the friction there between. This arrangement advantageously allows for manual rotation of the collar 330 without requiring excessive force.

As best seen in FIG. 6, the grooves 342 defined by the valve shuttle member 340 include a middle portion 343 that extends along a spiral or helical path (so that the rotations of the collar 330 drive longitudinal translation movements of the valve shuttle member 340). The grooves 342 also include an end portion 344 that extends circumferentially. This arrangement provides mechanical holding resistance between the collar 330 and the valve shuttle member 340 (so that when the valve shuttle member 340 is in the closed position, fluid pressure cannot overcome the mechanical holding resistance between the projections 332 and the end portions 344 that extend substantially orthogonal in relation to the longitudinal axis of the fluid coupling device 300). Accordingly, the valve shuttle member 340 in the closed position cannot be forced to open by fluid pressure in the fluid coupling device 300.

Figure 11:
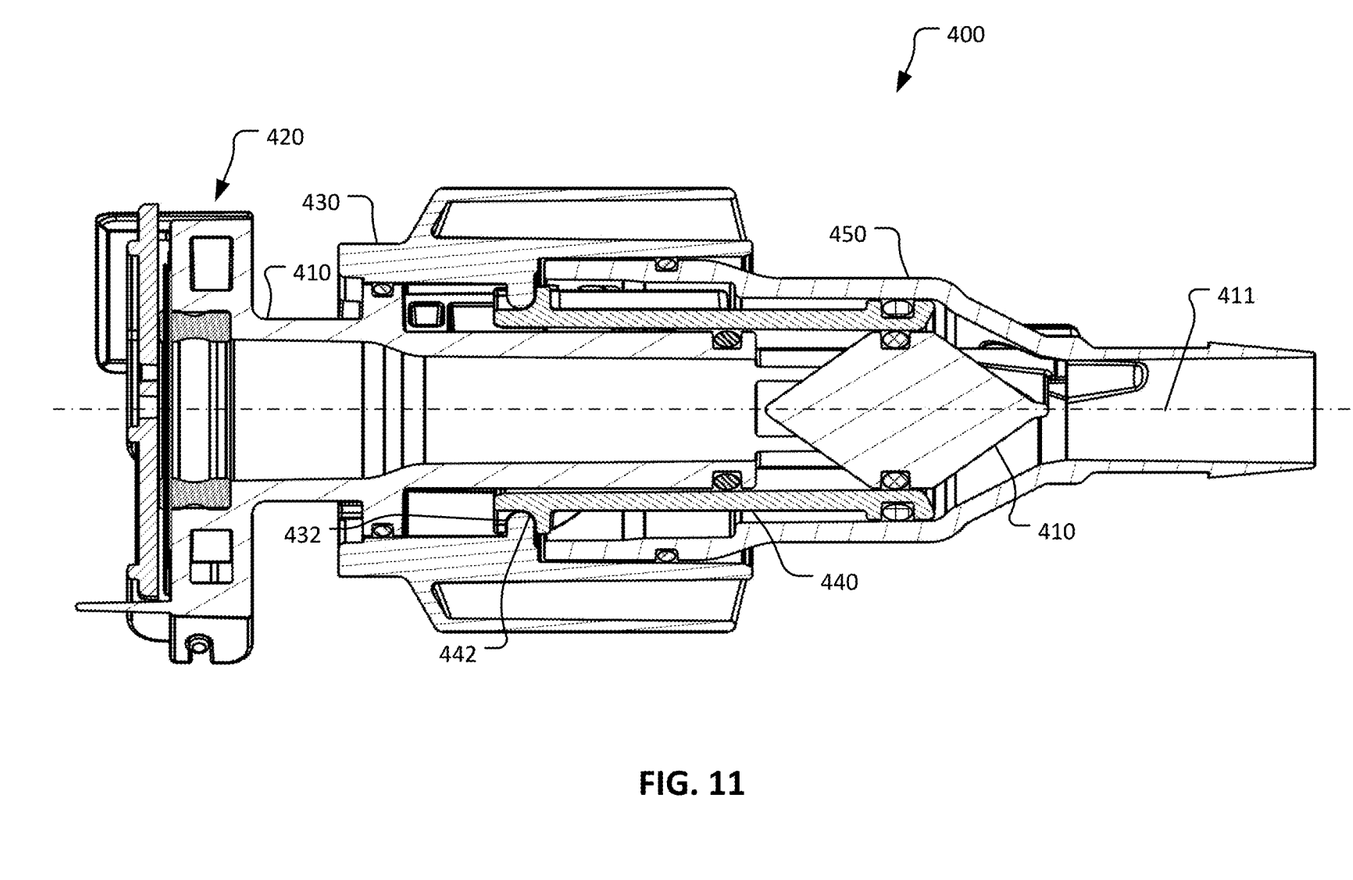
FIG. 11 is a longitudinal cross-sectional view of the fluid coupling of FIG. 10.
Figure 12:
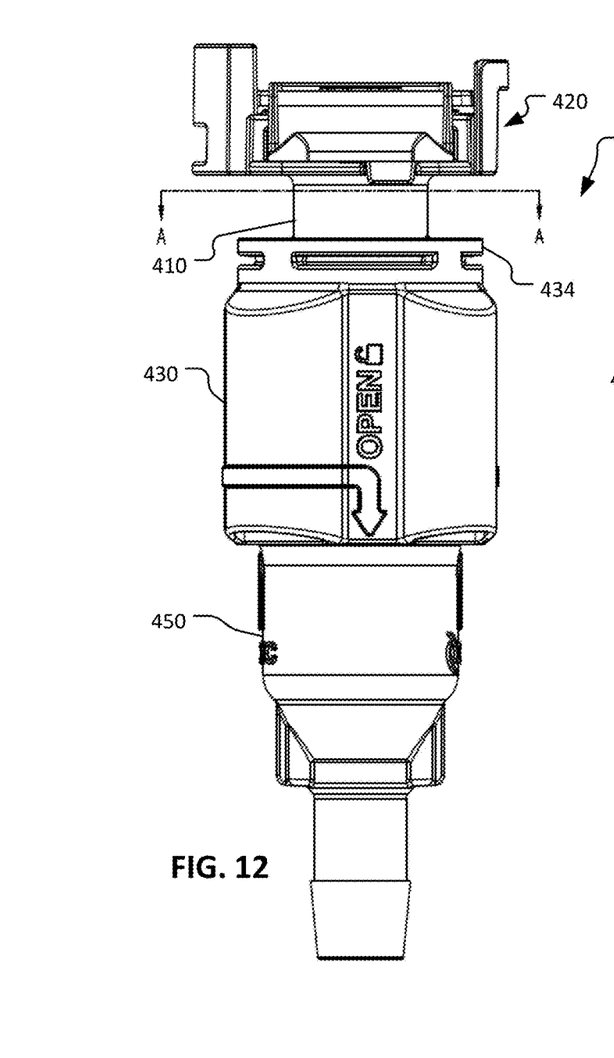
FIG. 12 is a top view of the fluid coupling of FIG. 10.
Figure 13:
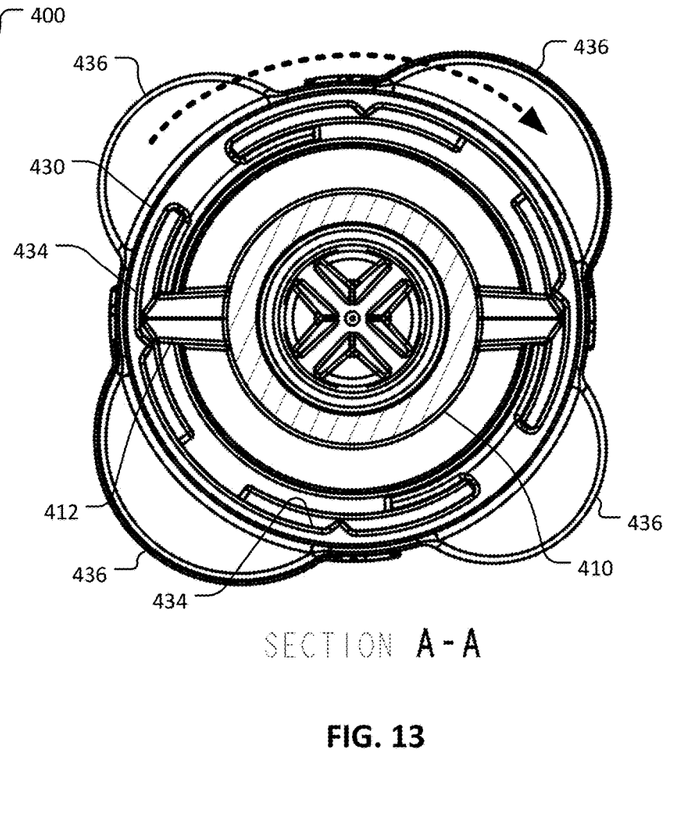
FIG. 13 is a transverse cross-section view taken along the cut plane A-A in FIG. 12.
Figure 14:
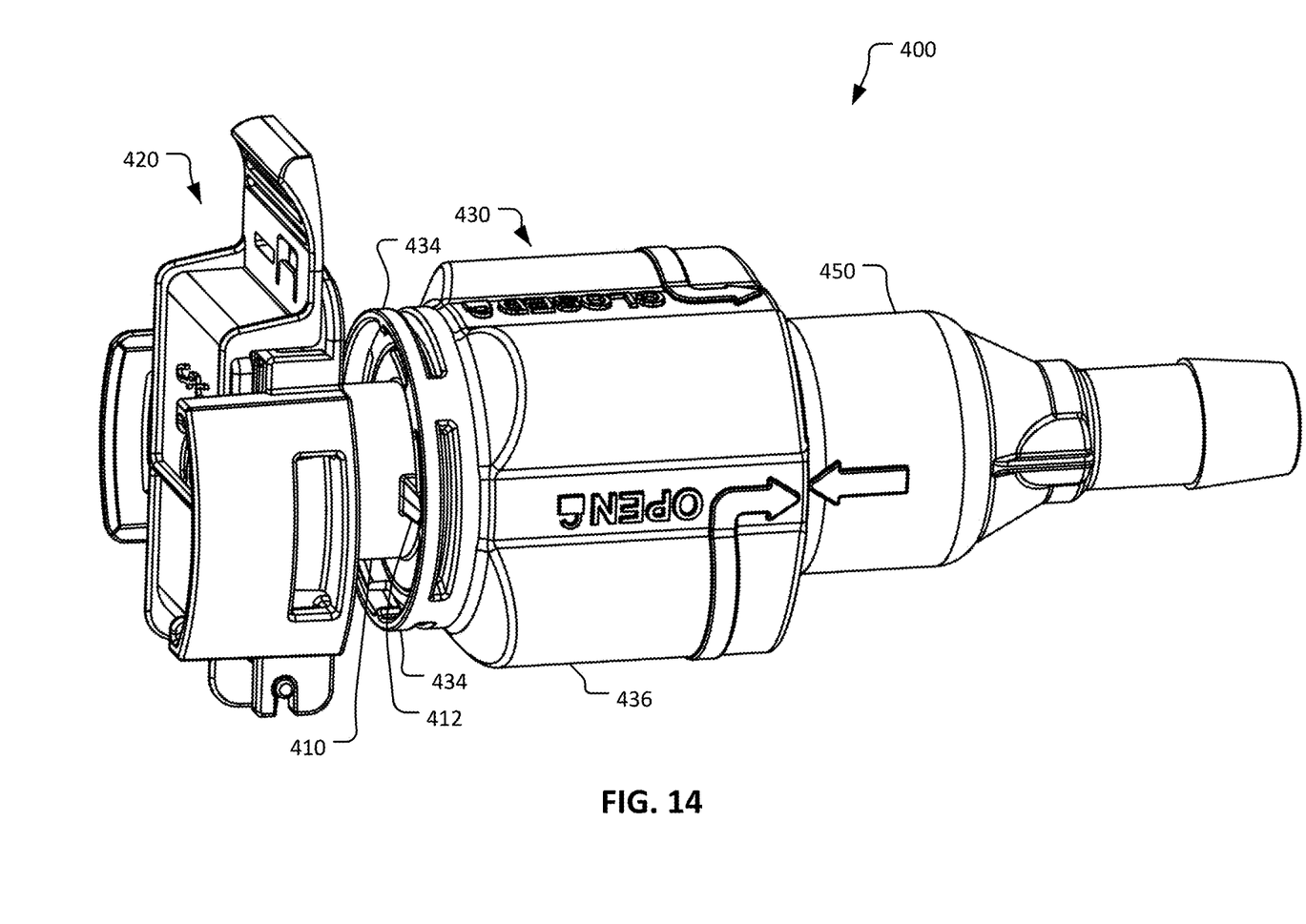
FIG. 14 is another perspective view of the fluid coupling of FIG. 10.

FIGS. 10-16 illustrate another example fluid coupling device 400. The fluid coupling device 400 includes a main body 410, an aseptic attachment structure 420 (including a protective cover and a removable membrane that is removably attached to a front face of the main body 410), a collar 430, a valve shuttle member 440, and a termination member 450. The main body 410 defines a longitudinal axis 411 (FIG. 11). In some embodiments, the component of the fluid coupling device 400 are the same as the fluid coupling device 300 except for the design of the collar 430 (versus the collar 330 of the fluid coupling device 300).

Figure 15:
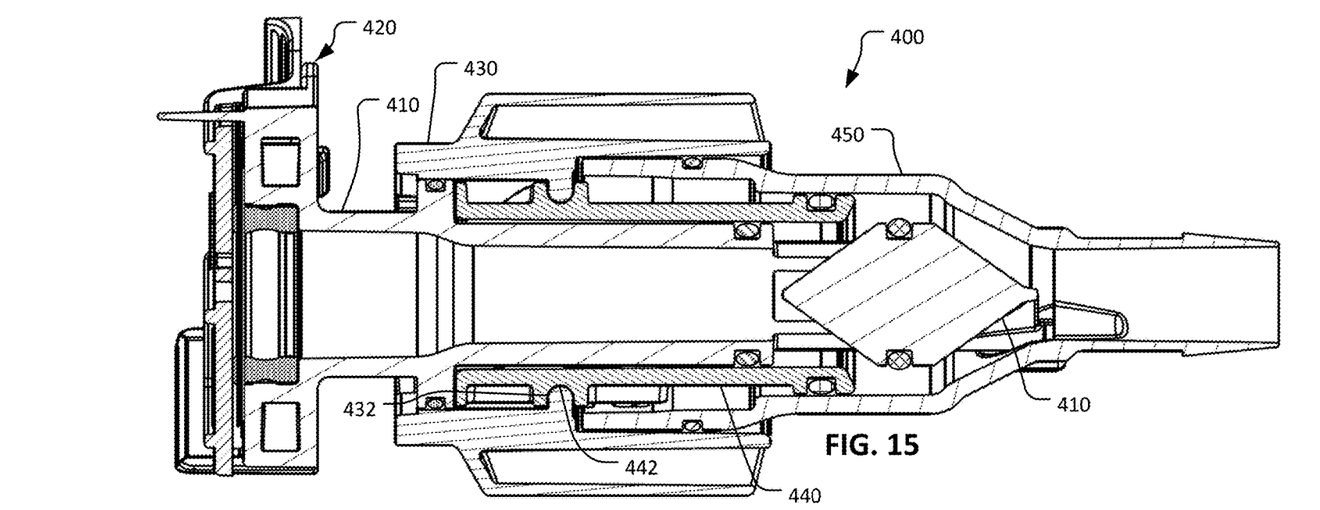
FIG. 15 is another longitudinal cross-sectional view of the fluid coupling of FIG. 10.
Figure 16:
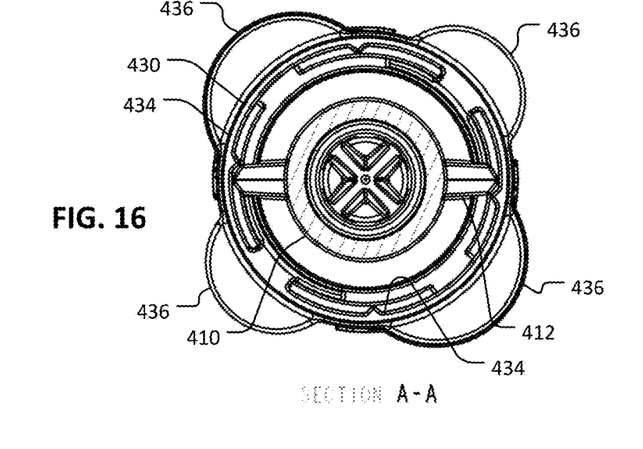
FIG. 16 is another longitudinal cross-sectional view of the fluid coupling of FIG. 10.

The collar 430 is rotatably coupled to the main body 410 and the termination member 450. Rotation of the collar 430 relative to the main body 410 drives longitudinal translational movements of the valve shuttle member 440 along the longitudinal axis 411 relative to the main body 410 and the termination member 450. Accordingly, rotation of the collar 430 moves the valve shuttle member 440 between a closed position (as shown in FIG. 11) in which the valve shuttle member 440 blocks fluid from flowing into and/or through the main body 410 and an open position (as shown in FIG. 15) in which fluid can flow through the fluid coupling device 400.

In the depicted embodiment, the collar 430 includes multiple lobes 436. There are four lobes 436 in this particular embodiment. In some embodiments, there are two, three, or more than four lobes 436. In the depicted embodiment, the lobes 436 are arcuate (convex) projections that extend radially on the outer periphery of the collar 430. In some embodiments, the lobes 436 can be polygonal, semi-cylindrical, triangular, and the like. The lobes 436 facilitate a good grip on the collar 430 so that a user can readily rotate the collar 430. The radial extension aspect of the lobes 436 also provide for applying a greater level of torque when rotating the collar 430.

The aseptic attachment structure 420 is configured to facilitate an aseptic connection to a second compatible fluid coupling device (not shown). In some embodiments, the second fluid coupling device can be another fluid coupling device 400. In some embodiments, the second fluid coupling device can be a different type of fluid coupling (as long as it has an aseptic attachment structure that is compatible with the aseptic attachment structure 420).

In the depicted embodiment, the collar 430 can be rotated to open and/or close the valve shuttle member 440 as many times as a user desires. In some embodiments, the collar 430 can only be rotated to the position the valve shuttle member 440 in its open position a single time. In such a case, the valve shuttle member 440 can latch/lock to be detained in its open position.

The collar 430 and the termination member 450 include markings in the depicted embodiment. The markings indicate whether the valve shuttle member 440 is in the open position, the closed position, or somewhere in between. The markings also indicate which way the collar 430 should be rotated in order to move the valve shuttle member 440 to a desired position (e.g., either open or closed).

In the depicted embodiment, the collar 430 includes four flexible collar portions 434 (e.g., see FIGS. 10, 12, 14 and 16) that each include a radially inward extending projection. The main body 410 includes two projections 412 that extend radially from the main body 410 and interface with the four flexible collar portions 434. The interactions between the projections 412 and the four flexible collar portions 434 create a detent mechanism that is reversible (applying enough torque or force can overcome the detent), and/or a latching mechanism that is locked and not reversible, between the collar 430 and the main body 410 at the end limits of rotational travel of the collar 430 relative to the main body 410. The end limits of rotational travel of the collar 430 relative to the main body 410 also correspond to the fully open and fully closed positions of the valve shuttle member 440 relative to the main body 410 and the termination member 450.

In some embodiments, the connection sequence for mating the fluid coupling device 400 to a second compatible aseptic fluid coupling is as follows. First, the fluid coupling device 400 starts with its valve shuttle member 440 in its closed position (FIG. 11). Then, using the aseptic attachment structure 420, an aseptic connection is made between the fluid coupling device 400 and a second compatible aseptic fluid coupling. Then, the user rotates the collar 430 to translate the valve shuttle member 440 to its open position (FIG. 15) to allow fluid to flow through the fluid coupling device 400.

As the collar 430 is rotated, two projections 432 on the collar 430 slide along two corresponding grooves 442 defined by the valve shuttle member 440 (in the manner described above in reference to the projections 332 and grooves 342 of the fluid coupling device 300). As with the projections 332 and grooves 342 of the fluid coupling device 300, in the depicted embodiment of the fluid coupling device 400, the end portions of the projections 432 are hemispherical and the grooves 442 have a corresponding semi-circular cross-sectional shape. This arrangement provides a semi-circular line contact between the collar 430 and the valve shuttle member 440 that minimizes the friction there between. This arrangement advantageously allows for manual rotation of the collar 430 without requiring excessive force.

In the same manner as the grooves 342 (refer to FIG. 6), the grooves 442 defined by the valve shuttle member 440 include a middle portion that extends along a spiral or helical path (so that the rotations of the collar 430 drive longitudinal translation movements of the valve shuttle member 440). In some embodiments, the middle portion extends along an angle in a range of about 30° to 40° relative to the longitudinal axis 411. In some embodiments, the middle portion extends along an angle in a range of about 20° to 50°, or about 20° to 40°, or about 30° to 50°, or about 10° to 60°, or about 10° to 30°, relative to the longitudinal axis 411. The grooves 442 can also include an end portion that extends circumferentially (in the same manner as the grooves 342). This arrangement provides mechanical holding resistance between the collar 430 and the valve shuttle member 440 (so that when the valve shuttle member 440 is in the closed position, fluid pressure cannot overcome the mechanical holding resistance between the projections 432 and the end portions 444 that extend substantially orthogonal in relation to the longitudinal axis 411 of the fluid coupling device 400). Accordingly, the valve shuttle member 440 in the closed position cannot be forced to open by fluid pressure in the fluid coupling device 400.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination. Other embodiments are within the scope of the following claims.

What is claimed is:

1. A fluid coupling device comprising:
a main body defining a longitudinal axis and including a front face that defines an opening to an interior space defined by the main body;
an aseptic attachment structure at a first end of the fluid coupling device and including a membrane that is removably attached to the front face and covering the opening to the interior space;
a collar that is rotatably coupled to the main body, the collar including a projection extending radially inward;
a valve shuttle member, at least a portion of the valve shuttle member being disposed between the collar and the main body, the valve shuttle member defining a groove in which the projection is slidably disposed such that manual rotation of the collar drives translation of the valve shuttle member along the longitudinal axis; and
a termination member coupled to the main body at a second end of the fluid coupling device that is opposite of the first end,
wherein the main body includes two radially outward extending projections, and wherein the collar includes four flexible collar portions that each interface with the two radially outward extending projections as the collar is rotated relative to the main body.

2. The fluid coupling device of claim 1, wherein the valve shuttle member is translatable along the longitudinal axis between a closed position that blocks fluid from flowing through the main body and an open position that allows fluid to flow through the main body.

3. The fluid coupling device of claim 1, wherein the groove includes a circumferential portion that extends circumferentially around the longitudinal axis.

4. The fluid coupling device of claim 3, wherein the groove includes a portion that extends along an angle of 30° to 40° relative to the longitudinal axis.

5. The fluid coupling device of claim 1, wherein the collar includes multiple lobes that extend radially outward from the collar.

6. The fluid coupling device of claim 1, wherein the collar includes four lobes that extend radially outward from the collar.

7. The fluid coupling device of claim 1, further comprising markings that indicate whether the valve shuttle member is in: (i) a closed position that blocks fluid from flowing through the main body and (ii) an open position that allows fluid to flow through the main body.

8. The fluid coupling device of claim 7, wherein the markings further indicate a direction to rotate the collar in order to move the valve shuttle member toward the close position and toward the open position.

* * * * *